United States Patent
Krivitski et al.

(10) Patent No.: US 6,746,408 B2
(45) Date of Patent: Jun. 8, 2004

(54) METHOD OF BLOOD FLOW MEASUREMENT IN ARTERIO-VENOUS HEMODIALYSIS SHUNTS BY INDICATOR DILUTION

(75) Inventors: Nikolai M. Krivitski, Ithaca, NY (US); Cornelis J. Drost, Ithaca, NY (US)

(73) Assignee: Transonic Systems Inc., Ithaca, NY (US)

( * ) Notice: Subject to any disclaimer, the term of this patent is extended or adjusted under 35 U.S.C. 154(b) by 0 days.

(21) Appl. No.: 09/867,102

(22) Filed: May 29, 2001

(65) Prior Publication Data

US 2002/0183632 A1 Dec. 5, 2002

(51) Int. Cl.[7] .................................................. A61B 5/02
(52) U.S. Cl. .................. 600/505; 600/504; 600/309; 604/503
(58) Field of Search ............................... 600/505, 526, 600/504, 507, 309; 604/28–29, 31, 503–4, 4.01, 5.01, 6.16, 7, 8; 73/61.64, 61

(56) References Cited

U.S. PATENT DOCUMENTS

| | | | | |
|---|---|---|---|---|
| 3,726,269 A | * | 4/1973 | Webster, Jr. ................ | 600/526 |
| 3,915,155 A | * | 10/1975 | Jacobson et al. ............ | 600/505 |
| 4,236,527 A | * | 12/1980 | Newbower et al. ......... | 600/505 |
| 4,507,974 A | * | 4/1985 | Yelderman ............... | 73/861.06 |
| 4,595,015 A | * | 6/1986 | Jansen et al. ............... | 600/526 |
| 4,632,125 A | | 12/1986 | Webler et al. | |
| 4,651,751 A | | 3/1987 | Swendson et al. | |
| 4,745,928 A | | 5/1988 | Webler et al. | |
| 4,817,624 A | | 4/1989 | Newbower | |
| 5,056,526 A | | 10/1991 | Khalil | |
| 5,373,850 A | | 12/1994 | Kohno et al. | |
| 5,599,303 A | * | 2/1997 | Melker et al. ................ | 604/80 |
| 5,682,899 A | | 11/1997 | Nashef et al. | |
| 5,685,989 A | * | 11/1997 | Krivitski et al. ............ | 210/103 |
| 5,830,365 A | * | 11/1998 | Schneditz ................... | 210/739 |
| 5,833,645 A | * | 11/1998 | Lieber et al. ................ | 604/509 |
| 5,833,671 A | * | 11/1998 | Macoviak et al. .......... | 604/247 |
| 6,004,275 A | * | 12/1999 | Billiet ....................... | 600/505 |
| 6,036,654 A | * | 3/2000 | Quinn et al. ................ | 600/526 |
| 6,177,049 B1 | | 1/2001 | Schnell et al. | |
| 6,189,388 B1 | * | 2/2001 | Cole et al. ................ | 73/861.07 |
| 6,200,301 B1 | * | 3/2001 | Pfeiffer et al. .............. | 604/503 |
| 6,241,667 B1 | * | 6/2001 | Vetter et al. ................ | 600/407 |
| 6,264,625 B1 | * | 7/2001 | Rubenstein et al. .......... | 604/9 |
| 6,287,273 B1 | * | 9/2001 | Allers et al. ................ | 604/27 |
| 6,315,735 B1 | * | 11/2001 | Joeken et al. ............... | 600/500 |
| 6,394,961 B1 | * | 5/2002 | Pfeiffer et al. .............. | 600/505 |
| 6,575,927 B1 | * | 6/2003 | Weitzel et al. ................ | 604/8 |
| 6,582,656 B1 | * | 6/2003 | Steuer et al. ................ | 422/44 |
| 6,623,436 B2 | * | 9/2003 | Krivitski et al. ............ | 600/505 |

OTHER PUBLICATIONS

William Ganz, M.D., et al. Measurement of Coronary Sinus Blood Flow by Continuous Thermodilution in Man. Dept.of Cardiology, Cedars–Sinai Medical Center, vol. XLIV, Aug. 1971.

V. Ganz, M.D. et al. Measurement of Blood Flow in the Femoral Artery in Man at Rest and during Exercise by Local Thermodilution. Institute for Cardiovascular Research, Prague, Budejovica, Czechoslovakia.

* cited by examiner

*Primary Examiner*—Henry Bennett
*Assistant Examiner*—Amanda Flynn
(74) *Attorney, Agent, or Firm*—Brian B. Shaw, Esq.; Stephen B. Salai, Esq.; Harter, Secrest & Emery LLP (57) ABSTRACT

The present invention provides a method for measuring the blood flow rate within an A-V shunt via indicator dilution techniques. Unknown flow resistance within the A-V shunt are addressed by adjusting a measured flow rate to provide a flow rate within a predetermined margin of error. The calculated flow rate can be rejected based upon flow conditions of the introduced indicator. Different indicator introduction rates can be used to enhance accuracy of the measured flow. The indicator flow path can include a flow restrictor to limit the flow rate of the indicator to below a predetermined value.

29 Claims, 2 Drawing Sheets

METHOD OF BLOOD FLOW MEASUREMENT IN ARTERIO-VENOUS HEMODIALYSIS SHUNTS BY INDICATOR DILUTION

FIELD OF THE INVENTION

The present invention relates an apparatus and method for measuring fluid flow, and more particularly, to determining blood flow rates in hemodialysis arterio-venous (A-V) shunts by dilution techniques, including thermodilution.

BACKGROUND OF THE INVENTION

Hemodialysis is a process by which an artificial kidney replaces the function of a kidney in a patient. Blood is removed from the patient through a patient access such as an arterio-venous (A-V) shunt, passed through a dialyzer and returned to the patient access for normal circulation through the vascular system of the patient.

Arterio-venous shunts used in hemodialysis are surgically created by insertion of a specially designed tube (artificial graft or autologous vein) between a peripheral artery and a vein, or by connecting a peripheral artery to a vein to create a native (shunt) fistula. The A-V shunts are designed to supply blood for the dialysis process. Typically, hemodialysis needles are inserted into the A-V shunt during a hemodialysis session and the shunt must provide enough blood flow to allow the dialyzer to effectively perform blood purification.

Because the A-V shunt is seen as a foreign object by the body, in many cases the hemodynamic conditions increase the probability of stenosis development. The stenosis may thrombose if timely intervention such as angioplasty or surgery is not performed. During an angioplasty procedure, the radiologist tries to restore the flow by a procedure such as balloon angioplasty. An estimation of intervention success is usually based on an X-ray visual picture of the narrowing, rather than measurement of the flow that presumably has been restored. More than 20–30% of these costly interventions are not successful. That is, the patient access thromboses or the angioplasty did not change the flow rate or flow rate drops back to the initial value within one month.

Another problem exists when the blood flow in an A-V shunt (mostly in native fistulae) increases to a very high value such as 3 to 4 l/min (liters per minute). This high flow rate can be dangerous because of possible heart overload. In this situation the surgeon should intervene to decrease the blood flow. Such change must be well-controlled: if the flow rate is decreased too much, there is a risk of thrombosis in the shunt if the flow rate decrease is too small, the danger of heart overload remains.

So the need exists to determine the blood flow rate in A-V shunts during angioplasty, surgical and other interventions for immediate assessment of intervention quality.

Commonly used methods to measure blood flow rate in biomedical diagnostic and research applications include transit-time ultrasound, Doppler ultrasound, electromagnetic, nuclear magnetic resonance and x-ray fluoroscopy principles. However, it is difficult to use these procedures routinely during angioplasty procedure on an A-V shunt.

A well-accepted blood flow measurement technique employing indwelling catheters is the indicator dilution method, often named Stewart-Hamilton method, after the inventors who pioneered this family of methods in the late 19th and early 20th century. In this method, an additional element is introduced into or extracted from the blood stream, or a blood property is changed (the "indicator"). A calibrated sensor placed downstream from the point of indicator introduction measures the absolute concentration of the indicator. Via well-known equations, one can derive the flow rate. These methods are widely used for cardiac output measurement using pulmonary artery catheters.

Besides their use for cardiac output, the use of thermodilution methods is also known to measure blood flow in arteries [Ganz 64] and veins [Ganz 71]. An arterial system is characterized by high downstream flow resistance due to arterioles and capillaries. A venous system is characterized by high upstream flow resistance due to venulas and capillaries.

In contrast to arteries and veins, the flow resistance of A-V hemodialysis shunts is not concentrated in known upstream or downstream locations. Instead, the location of the flow resistance depends upon the condition of the A-V shunt. As a consequence, the injected indicator can alter flow in the shunt in an unknown manner. Additionally, the dynamic range of blood flow that should be measured in the A-V shunt can vary approximately 100 fold (50 ml/min–5000 ml/min). Thus, the measurement of flow in A-V shunts involves special requirements that do not exists in natural arterial and venous systems.

Therefore, a need exists for determining the blood flow rate in an A-V shunt having a relatively large dynamic range of blood flow rates during the angioplasty, surgical and other interventions, for immediate assessment of intervention quality. The need also exists for a method and apparatus for determining the blood flow rate in an A-V shunt without requiring extensive retraining of personnel.

SUMMARY OF THE INVENTION

The present invention provides a method and apparatus for measuring the blood flow rate within an A-V shunt, wherein indicator dilution techniques are employed. The present invention accommodates the unknown flow resistance within the A-V shunt by adjusting the measured flow rate to provide a flow rate within a predetermined margin of error.

The invention also provides for an improved measurement accuracy of A-V shunt flow rate by an adjustment based on measurement of the injected indicator flow.

The invention further provides for improved measurement accuracy of an A-V shunt flow rate by a system configuration, wherein the system determines, or measures, the flow rate of the injected indicator and rejects or accepts the measured flow rate in the A-V shunt based on the flow rate of the injected indicator.

The invention further discloses improving the measurement accuracy of A-V shunt flow rate by the introduction of the indicator at different flow rates.

The invention also contemplates the use of a flow restrictor in the indicator flow path, the flow restrictor selected to limit the rate of flow of the injected indicator. That is, the flow rate of the injected indicator is limited by the structure of the indicator flow path.

DETAILED DESCRIPTION OF THE PREFERRED EMBODIMENTS

Figure 1:
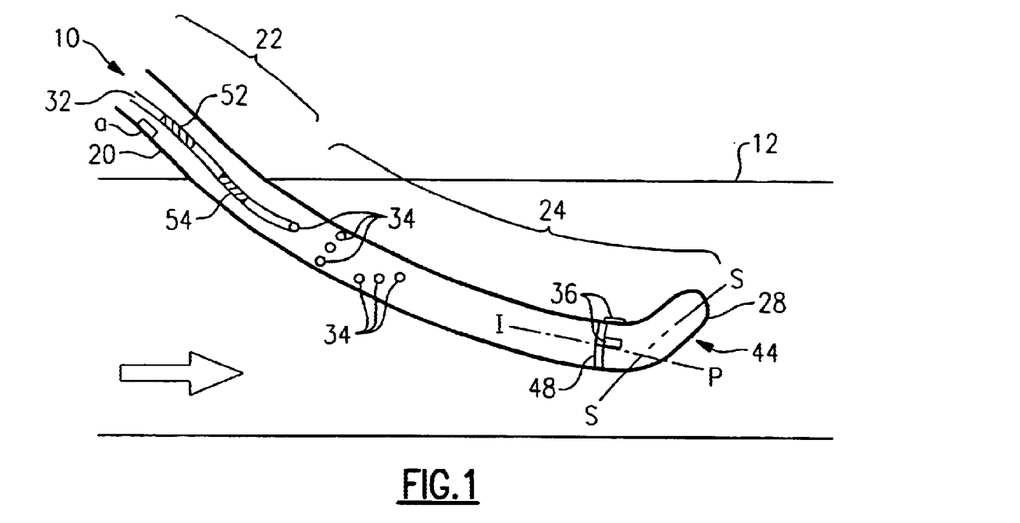
FIG. 1 is a cross sectional view of an indicator dilution catheter inserted in a vessel in the downstream direction of the blood flow and curved to reduce sensor contact with the vessel wall.
Figure 2:
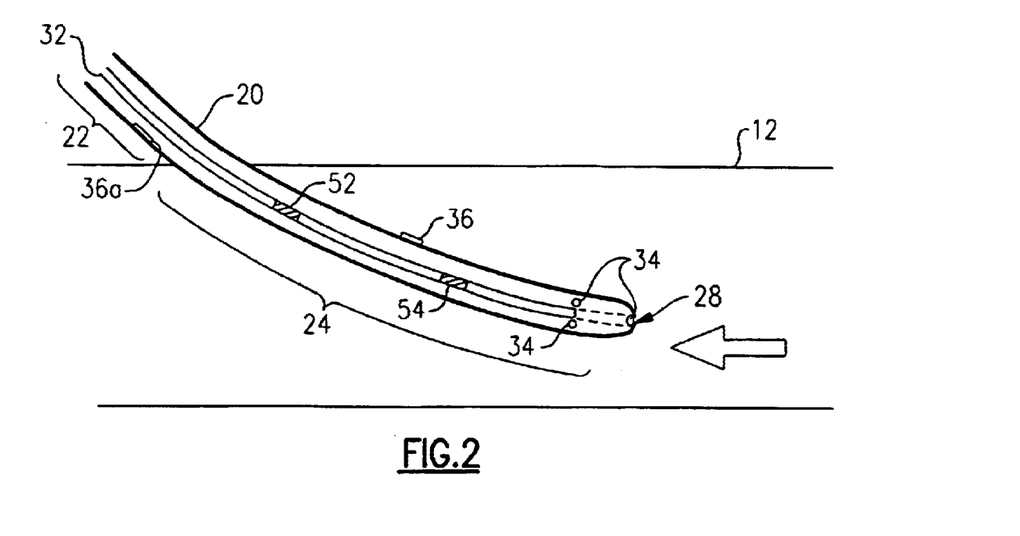
FIG. 2 is a cross sectional view of an indicator dilution catheter inserted in the vessel in the upstream direction, thus facing the blood flow.

Referring to FIGS. 1 and 2, the present indicator dilution catheter 10 is shown operably located in an arterio-venous (A-V) shunt 12. The A-V shunt 12 has a blood flow shown by the direction of the arrows, the catheter 10 includes an elongate body 20 having an extravascular portion 22 and an intravascular portion 24. The extravascular portion 22 being that portion or length of the body 20 that is not operably located within the A-V shunt 12 to contact the blood flow in the shunt. The intravascular portion 24 is that portion or length of the body 20 that is operably located within the A-V shunt 12 and contacts the blood flow in the shunt. The body 20 includes a proximal end, a distal end 28, an indicator lumen 32, an injection port(s) 34 and a sensor 36 (dilution sensor) for detecting passage of the injected indicator in the blood flow in the A-V shunt 12. Typically, the catheter 10 is operably connected to, or connectable to a controller. The controller can be a dedicated unit including hardware and software. Alternatively, the controller can be located as a portion of a hermodialysis system controller.

In operation, the indicator passes along the catheter 10 through the indicator lumen 32 to be introduced into the A-V shunt 12 blood flow through the injection port 34. The sensor 36 is typically connected to the controller via a lead or wire extending along the catheter 10.

It is important for the indicator dilution sensor 36 inside the blood stream to avoid contact with the A-V shunt wall or influence of the A-V shunt wall. To reduce the likelihood of the sensor 36 touching the wall, the special curvature of the catheter 10 as seen in FIG. 1 can be used. This curvature is selected to reduce the potential for contact between the sensor 36 and the A-V shunt wall. A length of the intravascular portion 24 of the body 20, and typically a length proximal to the distal end 28 of the body includes an inclined spacing section 44. The spacing section 44 has a longitudinal axis S—S that is non co-linear and non parallel to the longitudinal axis IP of an adjacent section of the intravascular portion 24. That is, the longitudinal axis of the spacing section 44 intersects the longitudinal axis of the adjacent section of the intravascular portion 24.

As the preferred configuration of the catheter 10 is directed to thermodilution, the sensor 36 is a thermal sensor such as a thermistor. Preferably, the sensor 36 has as small a volume as possible, so that the cross sectional area of the catheter 10 can be effectively minimized.

However, it is understood the thermal sensor 36 can be any sensor that can measure temperature, for example, but not limited to thermistor, thermocouple, electrical impedance sensor (electrical impedance of blood changes with temperature change), ultrasound velocity sensor (blood ultrasound velocity changes with temperature), blood density sensor and analogous devices. In fact, any parameter of blood that changes with temperature can be used to obtain thermodilution measurements.

The dilution sensors 36 detect a blood parameter and particularly variations of a blood parameter. For example, the dilution sensors 36 may be electrical impedance sensors, or optical sensors, the particular sensors being dependent on the blood characteristics of interest. Ultrasound velocity sensors, as well as temperature sensors and optical density, density or electrical impedance sensors can be used to detect changes in blood parameters. The operating parameters of the particular system will substantially dictate the specific design characteristics of the dilution sensor 36, such as the particular sound velocity sensor. If a plurality of dilution sensors 36 is employed, the sensors can be identical components. Ultrasonic sensors measure sound velocity dilution as the indicator material is carried past the sensor by the bloodstream, and changes in sound velocity are plotted to permit calculation of various blood parameters. The time at which the indicator material reaches the sensor 36 after injection, the area under the plotted curve representing the changes in sound velocity at the sensor, and the amplitude of the measurement all provide information concerning the blood characteristics.

Sensors 36 can be selected which register values or changes of any chemical or physical parameters of blood, these changes can correspond to a concentration within the blood flow in the A-V shunt 12. These embodiments can thus use, but are not limited to the following blood properties such as: blood electrical impedance, optical blood properties, blood temperature, blood density, blood pH, as well as blood ultrasound velocity. The sensors 36 in each embodiment include any type of sensor that records a corresponding measurement to such selected blood properties.

The indicator includes but is not limited to: blood hematocrit, blood protein, sodium chloride, dyes, blood urea nitrogen, glucose, lithium chloride and radioactive isotopes and microspheres. Any material that changes blood properties can be used as an indicator. The injectable indicator may be any of the known indicators including a temperature gradient indicator bolus.

Although the indicator introduction is shown as performed from the same catheter 10 in which the dilution sensor(s) 36 is (are) located, it is understood the indicator can be introduced through another separate catheter or through an introducer, or a needle.

Preferably, the indicator is injectable through the injection port 34. The injected (or introduced) indicator thus forms an indicator bolus.

The injected indicator, a liquid, can be a solution that is preferably non detrimental or minimizes any detriment to the patient, the blood of the patient, any blood components, and is non-reactive with the material of the system, including the material of A-V shunt. A preferred indicator is a solution such as isotonic saline and dextrose (glucose). However, it is understood any of a variety of solutions can be employed. Further, the term solution is taken to include single component injections.

The present analysis is set forth in terms of a reduced temperature indicator. That is, the indicator has a temperature below the temperature of the blood. However, it is understood that an elevated temperature indicator can be employed. That is, a temperature that is above the temperature of the blood in the A-V shunt.

The present invention provides for the determination of a volumetric flow rate ("flow rate") in an A-V shunt 12. The volumetric flow rate is a measure of the volume of liquid passing a cross-sectional area of the conduit per unit time, and may be expressed in units such as milliliters per min (ml/min) or liters per minute (l/min). A liquid flow having a flow rate also has a flow velocity, the distance traveled in a given time, such as millimeters per second (mm/s). Thus, for liquid flowing in an A-V shunt, there will be a flow rate (volumetric flow rate) having a flow velocity.

Blood flow rate (Q) can measured by thermodilution, using an indicator having a different temperature than the blood (typically through an injection of a liquid indicator), wherein the blood flow rate Q can be presented by the following formula:

$$Q = k(T_b - T_i)\frac{V}{S} \quad \text{(Equation 1)}$$

where $T_b$ is blood temperature in the vessel prior to injection; $T_i$ is the temperature of the injected solution prior it entering the blood stream; V [ml] is the volume of injected indicator; S [temp*time] is the area under the temperature versus time dilution curve resulting from the mixing of the injected indicator and the blood; and k is a coefficient related to thermal capacity of blood and the injected indicator. Typically, k is taken to be 1.08.

For continuous injections in Equation 1, V [ml/time] is the speed (rate) of the continuous injection, S is the temperature change of the blood due to mixing with the indicator, wherein the indicator can be colder/warmer than the blood.

A major difference between the classic dilution measurements of cardiac output and the measurements of blood flow rate in A-V shunts 12, wherein the indicator is introduced and a corresponding measurement is taken within a given section of the A-V shunt, is the absence of a mixing chamber such as the heart. That is, in classic dilution measurements of cardiac output, the blood and the indicator flow through the heart, which sufficiently mixes the indicator (thermal change) with the blood to provide reliable measurements.

However, if the blood and the indicator do not travel through a mixing chamber such as the heart, the design of the measurement system must provide for adequate mixing of the indicator with the blood within the space between the indicator introduction (injection) and the site of indicator dilution measurement.

The adequacy of mixing can be judged by comparing results of the dilution measurement with a more accurate method like, for example, volumetric timed collection of flow on the bench. If other sources of errors are controlled, the discrepancy between the measurement results can be contributed to inadequate mixing conditions.

Whether the mixing is adequate depends on the requirements of the clinical users and the dynamic range of the measured parameters. For example, for an angioplasty restoring procedure in A-V lower arm shunts, an average increase of the blood flow after angioplasty procedure is approximately 300–400 ml/min from 400–600 ml/min to 700–1000 ml/min. A measurement method would reliably indicate such procedural changes in flow, if its absolute error of flow measurement is less than the larger of 60–100 ml/min or 10%.

There are two different orientations for catheter placement in the A-V shunt 12. The A-V shunt 12 normally has a single flow direction, wherein blood flows from the arterial (upstream) side to the venous (downstream) side. Thus, the term downstream indicates directed with the flow, and the term upstream indicates directed against the flow.

1. Referring to FIG. 1, a catheter 10 is placed in the direction of blood flow, pointing downstream. In this case, the injected indicator enters the blood flow from a point along the catheter 10 or upstream of the catheter, and the indicator dilution temperature change can be recorded by the sensor 36 at or near the distal end 28 of the catheter 10.

2. Referring to FIG. 2, the catheter 10 is placed facing the blood flow, pointing upstream. In this case, if the injected indicator is introduced in the blood flow of the A-V shunt 12 via the same catheter, the indicator will first travel past the indicator dilution sensor 36 as the indicator passes along the indicator lumen 32. Alternately, the introduction of indicator could be made from a separate introduction site upstream of the indicator dilution sensor 36.

To enhance the accuracy of the measurements of blood flow rates using thermodilution, the following problems associated with specifics of thermodilution blood flow measurement within the A-V shunt 12 should be addressed:

(i) Supporting mixing conditions; and (ii) Reducing measurement errors resulting from the introduction of an indicator.

(i) Supporting Mixing Conditions

Various mechanisms can be implemented for enhancing the mixing conditions within the A-V shunt 12:

(a) Plurality of injection sites To create a uniform indicator distribution throughout the cross section of the flow in the A-V shunt 12, a plurality (two or more) of injection ports 34 for indicator introduction can be used. These injection ports 34 can be located on the same level or at different levels within, or across the cross sectional profile of the A-V shunt. These injection ports 34 can be located to face the flow, be with the flow or have spiral form or other forms, locations and configurations. It is preferable that the indicator pass through the catheter 10 in a single lumen or channel 32, from which the indicator is distributed to the plurality of injection ports 34. FIG. 1 depicts multiple configurations of arrays for the injection ports 34. It is understood a single array of injection ports would be employed in a catheter, and the multiple arrays in FIG. 1 are for illustration purposes. In FIG. 2, two locations of the injection port 34 (single port or in array form) are shown, again with the understanding a single configuration is employed in a given catheter 10. Specifically, the injection port 34 can be at the distal end 28 or proximal to the distal end.

(b) Plurality of dilution sensors To increase the accuracy of the measurements, especially in conditions where desired mixing may be difficult to achieve, a plurality of dilution sensors 36 can be used. The plurality of dilution sensors 36 are particularly applicable in conjunction with catheters having one port, a plurality ports, or a non volume indicator introduction such as the heating or cooling of the blood. In addition, a plurality of dilution sensors 36 can be employed when the indicator is introduced through a separate introducer, rather than the catheter on which the dilution sensors are located. Further, corresponding to the graph of FIG. 5 and seen in FIGS. 1 and 2, a sensor 36a can be located outside the A-V shunt 12 to provide the measurement of the passage of the indicator through the shunt. The flow rate $Q_c$ may be calculated from the individual dilution sensor measurement Q1, Q2, Q3, . . . for example, as follows. If the sensors are disposed about a circle or ring, simple averaging can be performed:

$$Q_c = \frac{(Q_1 + Q_2 + Q_3 + \ldots Q_n)}{n} \quad \text{(Equation 2)}$$

where n is the number of sensors. Alternatively, the area under the dilution curve associated with each sensor can be summed and averaged for determining the flow. As a further refinement, one could evaluate all individual sensor readings and discard one if its measurement indicates that the sensor is positioned against the vessel wall.

(c) Turbulent introduction of the indicator into the blood flow in the A-V shunt. The kinetic energy introduced into the initial blood flow Q by the injected indicator can enhance the mixing conditions by creating turbulence in the blood flow. This can be achieved by making the opening(s) 34 in the catheter 10 from where the indicator leaves the catheter and enters the blood stream sufficiently small so the indicator will "jet" into the flow at a higher velocity than the present blood velocity. It may be enhanced by angling these holes so the injection jet is directed against the direction of blood flow in the A-V shunt 12. It may be enhanced by the use of a plurality of holes spaced around the perimeter of the catheter, such as along a ring. However, for the jetting introduction, the injection ports 34 are sized to at least substantially preclude hemolysis in the A-V shunt 12.

(d) Use of a thermally conductive band. Placing a thermally conductive band 48 around the catheter at the site of the indicator dilution sensor 36 and in close thermal contact with the sensor. Such a band, typically constructed of metal, will assure that the indicator dilution sensor 36 will average the temperatures of a larger cross sectional area of the blood flow, and will thus partly offset variations in blood temperature that result from inadequate mixing. As the sensing will be done around the full perimeter of the catheter 10, such a band 48 will also reduce the loss in measurement accuracy that results when an un-banded indicator dilution sensor is positioned against the wall of the A-V shunt 12.

The distance between the injection port 34 and the sensor 36 are preferably selected to provide sufficient mixing of the introduced indicator and the blood. For the catheter 10 facing the flow, the distance between the port 34 and the sensor 36 is approximately 2 to 4 cm. For the catheter 10 oriented with the flow, the distance between the injection port 34 and the sensor 36 is approximately 3 to 6 cm.

(ii) Reduce Measurement Errors Resulting from the Introduction of an Indicator

The introduction of a volume of indicator at a flow rate $Q_i$ can change the initial flow rate Q. The effect of $Q_i$ depends on the particulars of the hemodynamic resistance of the A-V shunt 12.

In the arterial environments, the major resistance to flow is downstream where the downstream resistance may well exceed the upstream resistance 20–100-fold. Thus, the injected flow does not change the initial flow at the site of the sensor. During the injection period, the arterial inflow into the measurement site will temporarily reduce in response to the external injection. In this case, the recorded dilution curve will represent the initial blood flow rate, and the measured blood flow rate $Q_m$ will be close to initial blood flow:

$$Q_m = Q \quad \text{(Equation 3)}$$

In the venous environments, the main flow resistance is upstream from the measuring site, where the flow resistance may exceed the downstream flow resistance 20–100-fold. In this situation, the dilution measurement $Q_m$ will represent the sum of initial flow and injected flow:

$$Q_m = Q + Q_i \quad \text{(Equation 4)}$$

In A-V shunt systems 12 the location and distribution of the resistances is unknown. That is, the resistance to flow can be downstream in which the volume of the introduced indicator will effectively not be seen. Alternatively, the resistance to the flow in the A-V shunt 12 can be upstream, in which case the measured flow will include at least a portion of the flow rate of the introduced indicator. In the A-V shunt 12, the flow resistances will depend on factors such as initial surgical anatomical construction of the shunt, locations of stenoses and placement of the catheter. Thus, contrary to the arterial and venous environment, the relationship of the measured flow rate $Q_m$ in A-V shunts to initial blood flow rate is unknown. The measured flow rate $Q_m$ will be somewhere between initial flow Q and the initial flow plus injection flow $Q+Q_i$, depending on distribution of resistances in relation to the place of the injection. The range of uncertainty directly depends on the injection flow rate $Q_i$. Therefore, while a larger $Q_i$ is desirable for enhancing mixing conditions, the relatively large $Q_i$ may result in a less accurate flow measurement because of the unknown effect of $Q_I$ on the initial flow rate. The best flow rate $Q_i$ is a compromise: not too large, not too small. To minimize the error from the injection flow rate $Q_i$ being too large or too small, the following can be employed:

1. Calculating the flow rate $Q_c$ based on the injection flow rate $Q_i$ and on information of measurement conditions such as the type of the A-V shunt, the distribution of the resistances and the value of $Q_m$ itself.
2. Limiting the ability of operator to inject the indicator too quickly, while still providing sufficient ejection velocity to enhance mixing.
3. Rejecting the result of the flow measurement $Q_m$, if the flow rate of the injection $Q_i$ is too high or too low.
4. Employing two injection flow rates to gain a further improvement in shunt flow measurement accuracy and to reveal the location of the hemodynamically significant stenosis in the A-V shunt.

1. Calculating $Q_c$ by Adjustment of the Measured Value of $Q_m$

In high-flow, well developed native fistula, the major flow resistance (between 50% and 100%) is located at the arterial anastomosis. This means that the flow resistance downstream from the injection is between 0 and 50% of the total flow resistance. For this case the flow measurement error is reduced by using a flow calculation algorithm which places 75% of the flow resistance upstream from the point of indicator introduction, 25% downstream. The calculated flow $Q_c$ will then be:

$$Q_c = Q_m - 0.75 Q_i \quad \text{(Equation 5)}$$

In this case the possible error introduced by the injection flow will be less than 25% of $Q_i$.

In most well functioning lower arm artificial grafts, blood flow is in the range of 1000–1600 ml/min. The literature suggests again that the major flow resistance (between 50% and 100%) is located upstream from the catheter (arterial anastomosis, supplying artery). Therefore, equation 5 can be used.

Therefore, if the indicator dilution measurement of shunt flow is 1100–1200 ml/min or more the flow measurement device may be configured to automatically use Equation 5.

On the other hand, flow limiting stenoses in artificial grafts generally develop in the venous outflow side of the A-V shunt. Therefore, if the angiogram reveals that such is the case, another measurement algorithm for such specific instances can be used. Assuming that at least 50% of the flow resistance is now on the venous side, the algorithm could now be:

$$Q_c = Q_m - 0.25 Q_i \quad \text{(Equation 6)}$$

In this case the possible error introduced by the injection flow will again be less than 25% of $Q_i$.

In the general case when the distribution of hemodynamic resistances is unknown, one may minimize influence of injection flow on the flow reading reported to the operator through the use the following equation to calculate initial flow $Q_c$:

$$Q_c = Q_m - \frac{Q_i}{2} \quad \text{(Equation 7)}$$

In this case the error from the injected flow will be less than 50% of $Q_i$.

Figure 3:
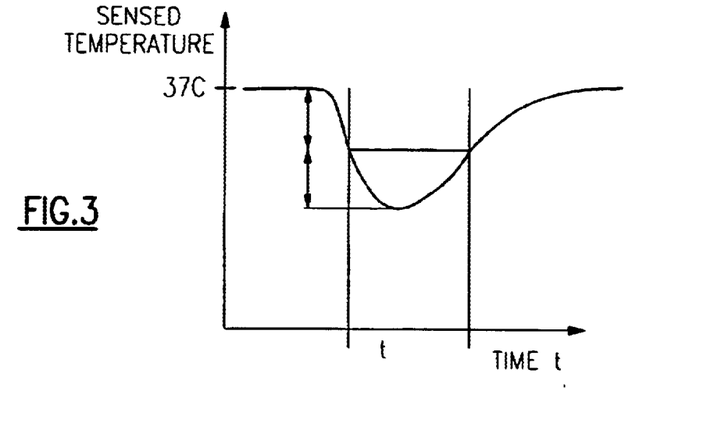
FIG. 3 is a graphical representation of the relationship between time and blood temperature by the indicator dilution sensor and measurement of injection time.
Figure 4:
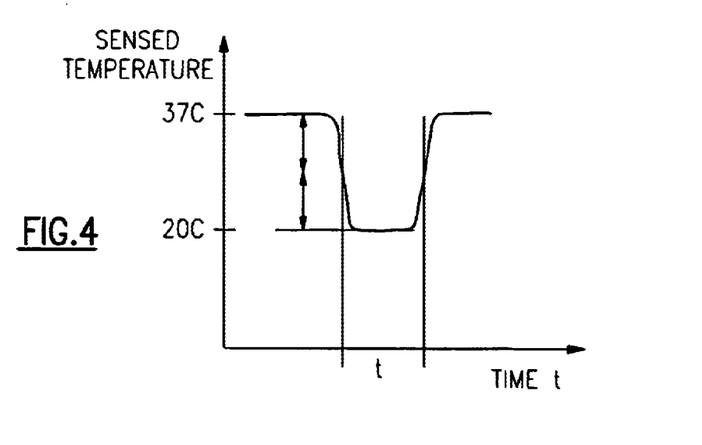
FIG. 4 is a graphical representation of the relationship between time and temperature by the injection temperature sensor and measurement of injection time, when such injection temperature sensor is located in a portion of the catheter in contact with the blood stream.
Figure 5:
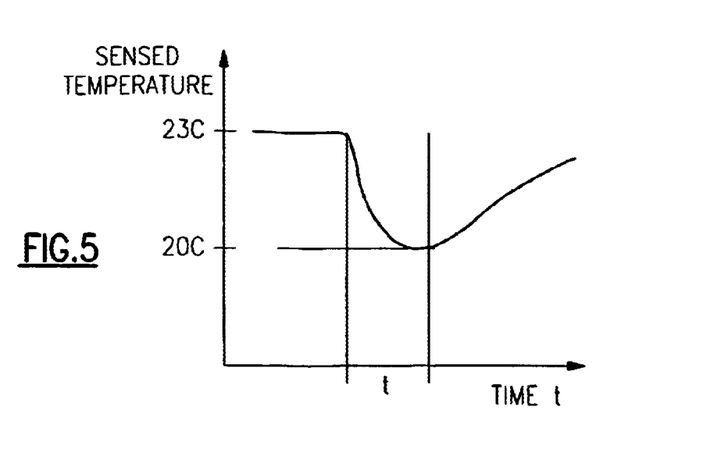
FIG. 5 is a graphical representation of the relationship between time and temperature by the injection temperature sensor and measurement of injection time, when such injection temperature sensor is located outside the blood stream and the body of the patient.

The value of $Q_i$ can be estimated, for example, as a ratio of known injected indicator volume (V) and time of injection (t):

$$Q_i = \frac{V}{t} \quad \text{(Equation 8)}$$

wherein the time of injection t can be estimated from the temperature curve of a thermal sensor. For example, the time t can be derived from the indicator dilution curve, from the width of that curve at its half height (FIG. 3), or from the time period between the beginning the bolus registration to the moment to the beginning of the downslope. Alternately, the time t can be derived from the curve from the injection thermal sensor by the time period between the beginning of the bolus to the beginning of the downslope (FIG. 4 and FIG. 5). Alternatively, if a dedicated indicator injection pump is used, the value of the injection time can be acquired from the pump setting.

2. Limiting the Ability of the Operator to Introduce the Indicator too Quickly

In practice, it is important to limit the ability of the operator to inject the indicator too quickly, thus introducing large flow changes. For example, in [Ganz 1964] the authors injected 5 ml of saline in 0.3–0.5 second, which results in an injected flow rate of Qi=600–1000 ml/min. This injected flow rate is unacceptable in A-V shunt flow measurements because the injected flow rate may exceed the actual flow in the shunt, thereby introducing large error. Thus, the speed of the indicator injection is a compromise between the need to achieve sufficient mixing (the higher injection flow the better chance of sufficient mixing) and the need to limit the flow rate of the indicator injection because of increase in error due to unknown distribution of resistances.

To limit the ability to inject too quickly, the indicator lumen 32 and/or injection port(s) 34 can be designed to be sufficiently small to increase the resistance to flow. That is, flow resistance of the indicator through the indicator lumen or the injection ports is selected to limit the injection rate.

For example the indicator lumen or the flow path of the indicator can include a tortuous flow path 52 which provides sufficient resistance to flow to preclude an injection flow rate greater than 200 ml/min. In a preferred configuration, the injection rate is between approximately 60 ml/min to 200 ml/min. The resistance is selected to provide the desired flow rate for, or within, normal anticipated pressures on the indicator. Also, the indicator may pass through a cellular structure 54 to create the desired flow resistance. It is also contemplated the injection port(s) 34 can be sized to create at least a portion of the flow resistance to limit the upper end of the indicator injection flow rate. In a preferred embodiment, the injection ports 34 of the catheter 10 may be dimensioned to serve this function.

As an alternate, flow-limitations may be programmed into an automated pump that provides controlled indicator injections. This pump can be programmed to repeat measurements if the pump rate is improper based on the measured rate of shunt flow, and repeat such measurements at a more optimal rate of pump flow.

3. Rejecting the Result of the Flow Measurement if the Injection Flow Rate is too High or too Small The rejection of the flow measurement if the introduced indicator flow rate is too small or too large can be accomplished by the controller operably connected to the sensor 36. The controller can include software for determining the length of time of the indicator injection and subsequently reject the measured flow rate, if the indicator flow rate was too great or too small. The controller can be configured to estimate an indicator injection rate, or rely upon an absolute time t of the injection. For example, if the 10 ml injection time t is less than 2 seconds (Qi>300 ml/min), the controller can reject the resulting measured flow rate. Further, if the if the injection time t is greater than 10 seconds (Qi<60 ml/min), the controller can reject the resulting measurement as the desired mixing may not have been achieved. Such controller may be structured to provide error warnings to the operator.

The window of injection times accepted by the controller can be selected to automatically take into account the A-V shunt flow reading. For instance, if the indicator dilution reading would be 2000 ml/min, an injection flow rate of 300 ml/min may still be acceptable. If the indicator dilution reading would be only 400 ml/min, the same 300 ml/min injection rate could create unacceptable measurement tolerances and an operator warning could be issued to redo the measurement at a slower injection rate.

4. Employing two Injection Flow Rates

Two successive indicator dilution measurements performed at different injection flow rates can be made to further increase the A-V shunt flow measurement accuracy and/or gain knowledge on whether the flow limiting stenosis in the shunt is located on the arterial or on the venous side of the shunt.

Analogous to equations 5–8, two injections with different injection flow rate $Q_{i1}$ and $Q_{i2}$ will produce two measured flow rates $Q_{m1}$ and $Q_{m2}$:

$$Q = Q_{m1} - p Q_{i1} \quad \text{(Equation 9)}$$

$$Q = Q_{m2} - p Q_{i2} \quad \text{(Equation 10)}$$

where p is the portion of injection flow that adds to the initial flow and should be subtracted from measured flow.

Equations 9 and 10 can be solved for the two unknowns p and the initial shunt flow Q:

$$Q = \frac{(Q_{m1} \times Q_{i2} - Q_{m2} \times Q_{i1})}{(Q_{i2} - Q_{i1})} \quad \text{(Equation 11)}$$

$$p = \frac{(Q_{m1} - Q_{m2})}{(Q_{i1} - Q_{i2})} \quad \text{(Equation 12)}$$

For accurate measurement of p and Q using Equations 11 and 12, the difference between the two injection rates, ($Q_{i2}$–$Q_{i1}$), should be as large as possible. That is, if $Q_{i2}$ and $Q_{i1}$ approach each other, the numerator becomes too large and thus introduces an unacceptable amount of error into the calculation.

Both indicator introductions, or one of them may be performed from the same catheter where dilution sensor(s) is (are) located, or through another catheter or through the introducer, or through a needle. Injections of different rates also can be done by the dedicated pump. In one embodiment, a slow injection can be performed through the catheter where flow is restricted, a quick injection can be performed through the introducer of this catheter (the "sheath"). One may also use a catheter with two separate channels (lumens) with different resistances for injection at different flow rate. Alternatively, one can use a catheter with one injection lumen, where the injection into this lumen takes place via a flow restricting valve with at least two positions.

In instances where it is impractical to inject at two flow rates that are sufficiently different to yield accurate values for Q and p in Equations 11 and 12, the two-injection method can still be used to eliminate some of the influence of the injection flow rate on the measurement and thus improve measurement accuracy. In this instance, one would only employ Equation 12 to find a rough estimation of the value p. If p is well below 50% one can conclude that the main flow resistance is located in the shunt downstream from the injection port(s). Therefore, the use of Equation 6 is indicated to calculate shunt flow $Q_c$; one should then calculate $Q_c$ using the indicator dilution measurement done at the lower injection flow rate. Conversely, if p is found to be substantially larger than 50%, the main flow resistance is likely located in the shunt upstream from the injection port(s). In this instance the use of Equation 5 is indicated for calculating $Q_c$ (again using the indicator dilution measurement made at the lower injection flow rate). If p is found to be near 50%, an intermediate injection flow correction ($Q_c = Q_m - 0.5 Q_i$) is appropriately used. In all these instances, the error introduced into the measurement of Q stemming from the injection flow is reduced to 25% of the injection flow.

The measurement of p in the above approach yields further information, helping the radiologist to select appropriate corrective procedures. As disclosed above, the value of p reveals whether the flow limiting stenosis is located upstream or downstream from the catheter's flow measurement site. It therefore informs the radiologist at which side of the shunts he/she should perform the flow-restoring procedure. At a small value of p and low shunt flow, the hemodynamically significant stenosis is located at the venous side of the shunt; for a large value of p and small shunt flow it is located at the arterial end.

Although the family of inventions disclosed herein is primarily described on the basis of a thermodilution catheter, the spirit of invention and equations 2–12 can be used for any dilution catheter. Further, the application need not be limited only to A-V shunts, but can be employed in any vessel, conduit or channel, where the amount of flow resistance and/or the location of the flow resistance in the flow path (relative to the injection site) is unknown. The flow measurement $Q_m$ can be made using any indicator dilution method without departing from the spirit of this invention. Measurement or determination of the injection flow $Q_i$ can be calculated from any dilution curve like (FIG. 3); from the measurement the signal of an injection sensor; from a dedicated indicator injection pump setting, or simply by dividing the volume of indicator as indicated on the injection syringe by the injection time as measured by stopwatch, or any other method know in the art. The calculated flow $Q_c$ can be determined from a flow measured by any method known in the art, and the exact correction factor used for $Q_i$ in such a calculation can vary in between 0 to 100% using without departing from the spirit of this invention. That is, $Q_m$ can be determined by any methodology, formula or derivation, whereupon the present invention of determining $Q_c$ can be performed by modifying the measured flow $Q_m$. It is also understood the dilution measurements can be made percutaneous. That is, the sensors 36a can be located outside of the vessel or shunt 12 to measure the indicator in the flow within the shunt, wherein the resulting measured flow can be modified by the present formulas and concepts. Thus, the sensors 36, 36a can be optical, electrical, impedance, ultrasound or other sensor that can provide measurements of the indicator within the shunt 12 percutaneously.

While preferred embodiments of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed is:

1. In a method of calculating an initial blood flow rate in an arterio-venous shunt from an introduced indicator to the initial blood flow, the improvement comprising:
    (a) reducing a measured flow rate in the arterio-venous shunt by a portion of a flow rate of the introduced indicator.

2. The method of claim 1, further comprising calculating the introduced indicator flow rate from a blood dilution curve and a known volume of the introduced indicator.

3. The method of claim 2, further comprising basing the introduced indicator flow rate on a width of a time versus blood parameter curve.

4. The method of claim 1, further comprising employing a thermal indicator as an introduced indicator.

5. The method of claim 4, further comprising calculating the introduced indicator flow rate from an injection dilution curve of an injection temperature sensor.

6. The method of claim 1, further comprising basing the value of the portion on the measured flow rate.

7. The method of claim 1, further comprising relating the value of the portion to a shunt flow rate-dependent fraction of the introduced indicator flow rate.

8. The method of claim 1, further comprising setting the value of the portion at 50% of the introduced indicator flow rate.

9. The method of claim 1, further comprising setting the value of the portion between 40 percent and 60 percent of the introduced indicator flow rate.

10. The method of claim 1, further comprising rejecting a calculation of an initial blood flow rate in response to an injection time greater than a predetermined time.

11. The method of claim 1, further comprising rejecting a calculation of an initial blood flow rate in response to an injection time less than a predetermined time.

12. The method of claim 1, further comprising rejecting a calculation of an initial blood flow rate in response to the introduced indicator flow rate being greater than a predetermined value.

13. The method of claim 1, further comprising rejecting a calculation of an initial blood flow rate in response to the introduced indicator flow rate being less than a predetermined value.

14. The method of claim 1, further comprising reducing the measured flow rate by less than 75% of the introduced indicator flow rate.

15. The method of claim 1, further comprising reducing the measured flow rate by 50% of the introduced indicator flow rate.

16. The method of claim 1, further comprising reducing the measured flow rate by 25% of the introduced indicator flow rate.

17. The method of claim 1, further comprising providing a second introduced indicator flow rate into the shunt.

18. The method of claim 17, further comprising determining a second measured flow rate corresponding to the second introduced indicator flow rate.

19. The method of claim 18, further comprising calculating an initial blood flow in response to the measured flow rate, the second measured flow rate, the introduced indicator flow rate and the second introduced indicator flow rate.

20. The method of claim 18, further comprising calculating an initial blood flow corresponding to the measured flow rate, the second measured flow rate, the introduced indicator flow rate and the second introduced indicator flow rate.

21. A method of adjusting a measured blood flow rate in an arterio-venous shunt by introducing a thermodilution indicator at a given flow rate into the shunt, the method comprising:

(a) subtracting a percentage of the given flow rate from the measured blood flow rate.

22. The method of claim 21, wherein subtracting a percentage of the given flow rate includes subtracting between 20 percent and 80 percent of the given flow rate.

23. In a method of determining an initial flow rate in a vessel by an introduced dilution indicator to the initial flow, the improvement comprising:

(a) reducing a measured flow rate in the vessel by a portion of a flow rate of the introduced dilution indicator.

24. The method of claim 23, further comprising rejecting the determination of an initial flow rate in response to an injection time greater than a predetermined time.

25. The method of claim 23, further comprising rejecting the determination of an initial flow rate in response to an injection time less than a predetermined time.

26. The method of claim 23, further comprising rejecting the determination of an initial flow rate in response to the introduced indicator flow rate being greater than a predetermined value.

27. The method of claim 23, further comprising rejecting the determination of an initial flow rate in response to the introduced indicator flow rate being less than a predetermined value.

28. A method of adjusting a measured flow rate in a vessel, the measured flow rate measured from introducing an indicator at a given flow rate into the vessel, the method comprising:

(a) subtracting a percentage of the given flow rate from the measured flow rate.

29. The method of claim 28, wherein subtracting a percentage of the given flow rate includes subtracting between 20 percent and 80 percent of the given flow rate.

* * * * *

UNITED STATES PATENT AND TRADEMARK OFFICE
CERTIFICATE OF CORRECTION

PATENT NO. : 6,746,408 B2
DATED : June 8, 2004
INVENTOR(S) : Krivitski, Nikolai M. and Drost, Cornelis J.

It is certified that error appears in the above-identified patent and that said Letters Patent is hereby corrected as shown below:

Column 3,
Line 38, "hermodialysis" should read -- hemodialysis --.

Column 6,
Line 55, insert -- of -- after "plurality".

Column 9,
Line 38, insert -- of -- after "between the beginning".

Column 11,
Line 25, "rate" should read -- rates --.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,746,408 B2  
APPLICATION NO. : 09/867102  
DATED : June 8, 2004  
INVENTOR(S) : Nikolai M. Krivitski and Cornelis J. Drost Page 1 of 1

It is certified that error appears in the above-identified patent and that said Letters Patent is hereby corrected as shown below:

In Column 1, line 5, beneath the title "METHOD OF BLOOD BLOW MEASUREMENT IN ARTERIO-VENOUS HEMODIALYSIS SHUNTS BY INDICATOR DILUTION" and above the heading "FIELD OF THE INVENTION", insert the following paragraph:

--This invention was made with government support under Phase I SBIR (Small Business Innovative Research) Grant #1 R43 DK55444-01 A2 awarded by the National Institutes of Health. The government has certain rights in the invention.--

Signed and Sealed this

Fourth Day of August, 2009

JOHN DOLL  
*Acting Director of the United States Patent and Trademark Office*